(12) United States Patent
Habenicht et al.

(10) Patent No.: US 6,344,442 B2
(45) Date of Patent: \*Feb. 5, 2002

(54) ZONA PELLUCIDA PROTEINS FOR CONTRACEPTION

(75) Inventors: Ursula-Friederike Habenicht, Berlin; Alessandro Lobbia, Glienicke, both of (DE)

(73) Assignee: Schering Aktiengesellschaft (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/194,062
(22) PCT Filed: May 22, 1997
(86) PCT No.: PCT/DE97/01092
  § 371 Date: May 3, 1999
  § 102(e) Date: May 3, 1999
(87) PCT Pub. No.: WO97/44358
  PCT Pub. Date: Nov. 27, 1997

(30) Foreign Application Priority Data

May 23, 1996 (DE) .......................... 196 22 289

(51) Int. Cl.$^7$ .................. A61K 38/10; A61K 38/04; C07K 17/705
(52) U.S. Cl. .................. 514/14; 514/15; 514/21; 530/300; 530/326; 530/327; 530/328; 530/350

(58) Field of Search ............. 514/2, 8, 12, 14, 514/15, 21; 530/300, 322, 326, 327, 328, 350, 395

(56) References Cited

U.S. PATENT DOCUMENTS

| | | | |
|---|---|---|---|
| 4,691,006 A | | 9/1987 | Stevens ..................... 530/324 |
| 5,626,846 A | | 5/1997 | Dean ....................... 424/184.1 |
| 5,658,876 A | * | 8/1997 | Crowley et al. ............... 514/2 |

FOREIGN PATENT DOCUMENTS

| | | | |
|---|---|---|---|
| EP | 117934 | * | 9/1984 |
| WO | 92/03548 | * | 3/1992 |
| WO | 94/22472 | * | 10/1994 |
| WO | 96/06113 | * | 2/1996 |

OTHER PUBLICATIONS

Lou et al. T Cell Peptide of a Self–Protein Elicits Autoantibody . . . J. Immunology. vol. 151, No. 10, pp. 5790–5799, Nov. 15, 1993.*

Millar et al. Vaccination with a Synthetic Zona Pellucida Peptide . . . Science, vol. 246, pp. 935–938, Nov. 17, 1989.*

* cited by examiner

*Primary Examiner*—Jeffrey E. Russel
(74) *Attorney, Agent, or Firm*—Millen, White, Zelano & Branigan, P.C.

(57) ABSTRACT

The present invention relates to the use of peptides which are derived from zona pellucida proteins and are used for contraception, and pharmaceutical formulations which contain the peptides without the peptides having an immunogenic effect.

15 Claims, No Drawings

ZONA PELLUCIDA PROTEINS FOR CONTRACEPTION

This invention relates to the use of peptides that are derived from zona pellucida proteins for contraception and for pharmaceutical formulations that contain these peptides, without these peptides having an immunizing action.

With the increase in world population, the need for efficient methods of contraception is also growing. In addition to oral contraceptives and spermicides, mechanical contraceptives are also available here, such as, for example, IUDs (intrauterine devices), vaginal rings, and condoms. Another approach is based on preventing fertilization by blocking the egg-sperm interaction. The sperm must penetrate the zona pellucida, an extracellular matrix that consists of glycoproteins and that surrounds the female gametes (the growing oocytes and the ovulated egg). This interaction takes place via a complex interplay of ligands, as well as sperm receptors on the part of the ovocyte or the sperm surface. The zona pellucida of the various mammalian species consists of three to four glycoproteins, which are normally referred to as ZP1, 2, and 3 or ZPA, B and C [Harris, J. et al.: Cloning and Characterization of Zona Pellucida Genes and cDNA's from Variety of Mammalian Species: The ZPA, ZPB and ZPC Gene Families. DNA Sequence: 4, 361–393, (1994)]. In mice, it has been described that the sperm bond first to ZP3 via O-bonded oligosaccharide chains, and the additional bond is probably mediated by ZP2. ZP3 seems to mediate not only the initial bond of the sperm to the zona pellucida, but also another decisive process for fertilization, the acrosome reaction [Dean, J.: Biology of Mammalian Fertilization. J. Clin. Invest.: 89, 1055–1059 (1992); Wassermann, P. M.: Regulation of Fertilization by Zona Pellucida Glycoproteins. J. Reprod. Suppl.: 42, 79–87, (1990)].

In view of the fact that the zona pellucida glycoproteins are unique in the ovary, exhibit antigenic properties, and are accessible to circulating antibodies during the intraovarian growth phase, the research has focused on the development of contraceptive vaccines on the basis of zona pellucida proteins [Naz, R. K. et al.: Development of Contraceptive Vaccines for Humans Using Antigen Derived from Gametes (Spermatozoa and Zona Pellucida) and Hormones (Human Chorionic Gonadotropin): Current Status. Human Reprod. Update: 1, 1–18, (1995); Millar, S. E. et al.: Vaccination with Zona Pellucida Peptides Produces Long-Term Contraception in Female Mice. Science: 246, 935–938, (1989)]. A phenomenon that was noted in almost all animals in the case of immunization with zona pellucida proteins is the induction of an oophoritis. Previously it was not possible to completely explain the reason for the occurrence of an oophoritis. In any case, the formation of an oophoritis makes the longer-term use of zona pellucida proteins or of peptides that are derived from these proteins appear problematical for contraceptive immunization.

There is therefore an urgent need for a new contraceptive that actively prevents fertilization by blocking egg-sperm interaction, without having an immunizing action.

It has now been found that the egg-sperm interaction is prevented by peptides that are derived from zona pellucida proteins.

This invention relates to the use of peptides that are derived from zona pellucida proteins for contraception, without these peptides having an immunizing action.

In another embodiment, this invention relates to the use of peptides that are derived from zona pellucida proteins, for the production of pharmaceutical formulations.

In another preferred embodiment, the peptides are derived from mouse protein or human ZP1, 2, or 3 protein.

In an especially preferred embodiment, peptides are derived from mouse protein or human ZP3 proteins.

In another especially preferred embodiment, the peptides are

| | |
|---|---|
| -RYPRQGNVSS- | (SEQ ID NO:1) |
| -TPSPLPDPNSSPY- | (SEQ ID NO:2) |
| -SRNRRHVTDEADVT- | (SEQ ID NO:3) |
| -CSNSSSSQFQIHGPR- | (SEQ ID NO:4) |
| -TRKCHSSSYLVSLPQ- | (SEQ ID NO:5) |
| -SQFQIHGPRQ- | (SEQ ID NO:6) |
| -TPT..PDQNASPY- | (SEQ ID NO:7) |
| -CGTPSHSRRQPHVMS- | (SEQ ID NO:8) |
| -SRNRRHVTEEADVT- | (SEQ ID NO:9) |
| -TRRCRTASHPVSASE- | (SEQ ID NO:10) |
| -SRRQPHVMSQ- | (SEQ ID NO:11) |

In another especially preferred embodiment, the peptides are

| | |
|---|---|
| -RYPRQGNVSS- | (SEQ ID NO:1) |
| -TPT..PDQNASPY- | (SEQ ID NO:7) |
| -SRNRRHVTDEADVT- | (SEQ ID NO:3) |
| -TRRCRTASHPVSASE- | (SEQ ID NO:10) |
| -SQFQIHGPRQ- | (SEQ ID NO:6) |

The synthesis of peptides was carried out according to Fmoc strategy [Carpino, L. A. and Han, G. Y. (1970) J. Amer. Chem. Soc. 92:5748–5749; Carpino, L. A. and Han, G. Y. (1972) J. Org. Chem. 37:3404–3409] on solid vehicles [Merrifield, R. B., (1963) J. Am. Chem. Soc. 85, 2149] on an automatic peptide synthesizer. Should the peptides carry a free C-terminus (COOH), HMP-resin [Wang, S. -W. (1973) J. Am. Chem. Soc. 95, 1328] would be used for the synthesis. Should the C-terminus be amidated ($CONH_2$), Rink amide resin [Rink, H., (1987) Tetrahedron Lett. 28, 3787] would be used. Should the peptides N-terminally carry a free amino group ($H_2N$-), the Fmoc protective group would be cleaved in the last synthesis cycle. Should the N-terminus be acetylated (Ac-), however, the amino group of the N-terminal amino acid could be reacted with acetic anhydride after Fmoc cleavage.

The cleavage of the protective groups was carried out for 0.1–1.5 g of peptide resin with:

0.75 g of phenol,
0.25 ml of ethanedithiol,
0.5 thioanisole
0.5 ml of $H_2O$
10 ml of trifluoroacetic acid and three hours of incubation while being stirred at 37° C. in a water bath.

Peptide isolation was carried out either by precipitation with tert-butylmethyl ether cold (ice bath) and subsequent centrifuging, or after spinning-in in a vacuum by precipitation with ether and subsequent filtering. After drying, the peptides were purified via HPLC as needed.

Execution of the Tests

I. In Vitro Fertilization

In vitro fertilization represents a test system that makes possible a first review of a contraceptive effect of substances. In this case, the possibility exists of studying whether the contraceptive effect can be attributed primarily to an inhibition of the sperm function(s) or to an inhibiting effect on the oocytes, or to the two above-mentioned effects.

I.1. Animal Material

Fertile female mice ($CB_6F_1$ strain) about 12 weeks of age; fertile male mice ($CB_6F_1$ strain) at least 14 weeks of age.

I.2. Preparation and Execution

Pyrex and bulb bottles are autoclaved.

The medium according to Brinster, Whitten and Wittingham

| Substance | mg/100 ml dd $H_2O$ |
|---|---|
| NaCl | 599.5 |
| KCl | 35.6 |
| $CaCl_2$ | 25.1 |
| $KH_2PO_4$ | 16.2 |
| $MgSO_4$ | 29.3 |
| $NaHCO_3$ | 208.4 |
| Glucose | 100 |
| Na-pyruvate | 11.2 |
| Na-lactate | 0.44 ml |
| Penicillin | 8.0 |
| Streptomycin Sulfate | 5.0 |
| Phenol Red | 0.5 |
| BSA | a) 0.3% |
|  | b) 2.0% |

The medium is then set at pH 7.4 with 0.5 M NaOH.

Sterile bulb bottles are exposed to gas with carbogen for 5 minutes, and the medium is then filtered into the latter (with a shelf life of no more than one week at 4° C.). To equilibrate the oil, 100 ml of paraffin oil (uvasol) is heated for 2 hours at 100° C. and finally cooled. After cooling, 20 ml of BWW/0.3% BSA is added and exposed to gas for 20 minutes with carbogen.

All instruments that are to be used are sterilized overnight at 140° C. The incubator is set at 37° C., 5% $CO_2$, and 95% $O_2$.

The small Petri dishes:
a) are filled with paraffin oil that is exposed to carbon gas and kept warm at 37° C. to produce oocytes.
b) are pipetted onto the bottom of the small dish with 0.5 ml of BWW/2% BSA for sperm capacitation (prepared before the removal of the tubes), covered with equilibrated oil, and kept at 37° C.
c) 0.1 ml of BWW/0.3% BSA, corresponding to the concentrations that are to be tested, is mixed with or without substance (control) for the fertilization (prepared after removal of the tubes), covered with equilibrated oil, and kept at 37° C.

I.2.1. Induction of Superovulation 10 injection units of PMS/0.1 ml are injected intraperi-cutaneously into the approximately 12-week-old fertile mice, and 54 hours later, 10 injection units of HCG/0.1 ml are administered.

I.2.2. Recovering Sperm a. In Mice

To recover sperm, a mouse buck is sacrificed, and the two epididymal appendages are removed and transferred into the prepared small Petri dishes [see above under b)]. The tissue parts are cut in the medium, so that the sperm can escape. The sperm are capacitated for one hour in the incubator.

After the capacitation time has been completed, the sperm are diluted 1:5 with BWW/0.3 BSA. For counting in the counting chamber, a 1:1 aliquot is diluted with doubly distilled $H_2O$. The desired sperm concentration is 40,000–80,000/0.1 ml.

b. In Humans

For the zona bonding test in humans, the ejaculate of normo-zoospermatocidal donor semen is prepared with use of SpermFertil$^{(R)}$ glass wool columns (Mello Ltd., FRG). The filtrates were washed and resuspended in HFT-HSA (HFT=human tubal fluid medium according to Quinn et al., supplemented with 10 mg/ml of human serum albumin=HSA).

I.2.3. Recovery of Oocytes a. In Mice

The animals are sacrificed 13 hours after the HCG injection, and the tubes are removed and transferred into the prepared small Petri dishes [see above under a)]. Pending further processing, the small dishes are kept at 37° C. on the warming plate. Under the stereomicroscope, the tubes that are in oil are pulled apart. In this case, the cumulus clouds pour out, which then are transferred into the prepared medium drops (two cumulus clouds per drop).

b. In Humans

All human oocytes are obtained from post mortem material. Provision is made at all times to ensure that all legal, ethical and moral guidelines during the entire process are strictly followed.

Unless otherwise indicated, the oocytes are stored in 36.6 mmol of HEPES buffer, pH 7.4, which contains 1.5 M MgCl2 and 0.1% PVP at 4° C.

I.2.4. In Vitro Fertilization 0.1 ml of dilute sperma-defined concentration is added to the oocytes that are in the medium drops and is incubated for 24 hours in the incubator at 37° C.

I.3 Evaluation

After incubating for 24 hours in the incubator, the following parameters are computed:
a) Number of complete oocytes
b) Number of divided oocytes
c) Number of undivided oocytes
d) Number of degenerated oocytes.

The fertilization rate corresponds to the number of divided oocytes per total number of intact oocytes.

II. Zona Bonding Assay

The sperm and oocytes are obtained as described in in vitro fertilization.

The oocytes that are obtained as under I.2.3. are taken up by a finely drawn Pasteur pipette, whose diameter must be somewhat smaller than the diameter of the oocytes, with a few $\mu$l of BWW medium. This process is repeated several times and finally causes the zonae pellucida to burst. The cytoplasmic portion of the ooctyes is released, and the isolated zona pellucida is collected for further tests and covered in 0.1 ml of BWW medium with equilibrated oil and kept at 37° C.

II.1 Zona Pellucida Bonding Test a) In Mice

The capacitated mouse sperm (see I.2.2) are preincubated for 15 minutes either with a solvent or the desired substance, and then 0.1 ml drops are added to the isolated zonae pellucidae, in such a way that the incubation volume is a total of 0.2 ml (under oil). About 20 zonae pellucidae are studied per drop. The sperm concentration per drop is between 10,000 and 30,000 per $\mu$l. Sperm and zonae are incubated for 45 minutes in an incubator (see Description under I.2). After the incubation period, the number of bonded sperm per zona is evaluated under an inverse microscope. The upper limit of the sperm, which have yet to be counted exactly, is 20 sperm per zona pellucida under control conditions.

b) In Humans

The experiments consist of three incubation drops that contain 10 μl of a standard HTF-HSA medium (see above) and 40 μl of working medium (see below). A specific number of oocytes (for TEM) or hemizonae for the bonding was added to each drop to ensure bonding. For the bonding experiments, a 10 μl sperm drop ($50 \times 10^6$/ml) was added to each drop, covered with mineral oil, and incubated for 4 hours at 37° C. in 5% $CO_2$. The statistical evaluation was done according to the non-parametric Mann-Whitney two-sample test.

Composition of the working medium: 20 μl of 5 mmol $NaH_2PO_4$ (adjusted with phosphoric acid), pH 2.5, plus 20 μl of a specially composed doubly-concentrated HTF-HSA medium, mixed at a ratio of 1:1 (vol/vol).

Composition of the doubly-concentrated HTF-HSA medium:

| Substance | Concentration |
|---|---|
| NaCl | 203.2 mmol |
| KCl | 9.38 mmol |
| $CaCl_2$ | 4.08 mmol |
| $KH_2PO_4$ | 0.74 mmol |
| $MgSO_4$ | 0.4 mmol |
| $NaHCO_3$ | 450.0 mmol |
| Glucose | 5.56 mmol |
| Na-pyruvate | 0.66 mmol |
| Na-lactate | 42.8 mmol |
| Penicillin | 120 μg/ml |
| Phenol Red | 5 μg/ml |

Application

The above-mentioned peptides can be used in different pharmaceutical products.

Peptides can be administered invasively (intravenously, intramuscularly, subcutaneously, subdermally) and non-invasively (topically, orally). To achieve a lasting effect, long-term applications are of special advantage.

a) Formulation of Peptides as Microcapsules

Copolymers of lactic acid and glycolic acid are often used as microencapsulating material. This compound embeds the peptide. The microcapsules themselves are suspended in liquid waxes and oils such as isopropyl myristrate or castor oil.

b) Formulation as Salts

Basic cationic peptides can also form salts with anionic polymers, such as polyester, which are water-insoluble and are therefore suspended in a stable manner in aqueous vehicles.

c) Biodegradable Implants

The materials that are mentioned under a) and b) can also be extruded or pressed. Large shaped bodies are produced, which represent subdermal active ingredient deposits for use for periods of 6 months to 6 years.

d) Liposomes can also be used as vehicles for peptides. The shell is preferably made of phosphatidylcholine and cholescol and optionally other components that are largely impermeable to the active ingredient. Thus, the latter is optimally protected. The liposomally encapsulated peptides can be administered both inversively and topically or orally.

e) TDS are especially suitable for the indication provided. They are used for, e.g., 7 days, and release the active ingredient constantly. As a skin contact adhesive, all commonly used silicone and acrylate adhesives can be used. The addition of a commonly used enhancer to cross the skin barrier may be important. The formulation principle can be used up to a molecular weight of 1000 Dalton and thus is especially suitable for the peptides that are described.

f) Mucous membrane-adhesive systems are suitable especially for transmucosal and transnasal use. As is generally known, this barrier with peptides is easier to cross than the skin. In addition, enhancers can be used here. As forms of administration, powders and solutions (sprays) and ointments of all types are suitable.

g) As already reported under f), peptides find it difficult to pass through the skin, and use as creams, gels or ointments is possible in the uncharged state for smaller molecules. Disposable packages are desirable with a view to safer use.

h) Charged peptides can be administered into the skin using iontophoresis. A corresponding device consists of 2 parts, a donor-gel side with electrodes and a counterpol, where the active ingredient is delivered to the skin with donor voltage applied.

Other pharmaceutical formulations are possible with the commonly used adjuvants and vehicles.

EXAMPLES

Example 1

% Inhibition of Sperm Bonding (Mouse) to the Mouse Zona Pellucida

| ZPC Peptide | Remarks | 0.1 μg/ml | 1 μg/ml | 10 μg/ml | 100 μg/ml |
|---|---|---|---|---|---|
| $NH_2$-RYPRQGNVS S-COOH (SEQ ID NO: 1) | hu (141–150) | 71 | | 89 | 91 |
| $NH_2$-TPT..PDQN ASPY-COOH (SEQ ID NO: 7) | hu (220–230) | 100 | | 100 | 99 |
| $NH_2$-SQFQIHGPR Q-COOH (SEQ ID NO: 6) | m (334–343) | | | 61 | 72 |
| Ac-SQFQIHGPR Q-$NH_2$ (SEQ ID NO: 6) | m (334–343) | | | | |
| Ac-QRPGHIQFQ S-$NH_2$ (reverse) (SEQ ID NO: 12) | m (334–343) | | | 0 | 0 |
| Ac-/$NH_2$-(random) | m (334–343) | | | 0 | 0 |
| $NH_2$-SRNRRHVTE EADVT-COOH (SEQ ID NO: 9) | hu (348–361) | 69 | | 85 | 82 |
| $NH_2$-TRRCRTASH PVSASE-COOH (SEQ ID NO: 10) | hu (410–424) | 86 | | 87 | |

10,000 Sperm per 0.01 ml with 20 sperm bonds per zonae corresponds to 100%

Example 2

% Inhibition of Mouse In Vitro Fertilization

| ZPC Peptide | Remarks | 0.1 µg/ml | 1 µg/ml | 10 µg/ml | 100 µg/ml |
|---|---|---|---|---|---|
| SQFQIHGPRQ NH$_2$ COOH (SEQ ID NO: 6) | m (334–343) | | 52 | 29 | 1 |
| Ac-SQFQIHGP RQ-NH$_2$(SEQ ID NO: 6) | m (334–343) | | 0 | 63 | 5 |

Example 3

% Inhibition of Sperm Bonding (Human) to the Human Zona Pellucida

| ZPC Peptide | Remarks | 1 µg/ml | 10 µg/ml |
|---|---|---|---|
| NH$_2$-RYPRQGNVSS COOH (SEQ ID NO: 1) | hu (141–150) | 76 | 77 |
| NH$_2$-TPT..PDONASPY-COOH (SEQ ID NO: 7) | hu (220–230) | 0 | 18 |
| Ac-CGTPSHSRRQPHVMS-NH$_2$ | hu (327–341) | 45 | 88 |
| NH$_2$-SRNRRHVTEEADVT-G COOH (SEQ ID NO: 9) | hu (348–361) | 0 | 0 |
| NH$_2$-TRRCRTASHPVSASE-COOH (SEQ ID NO: 10) | hu (410–424) | 61 | 88 |

The peptides hu (141–150) and hu (327–341) do not trigger the acrosome reaction in capacitated human sperm.

The peptide hu (141–150) does not influence any parameters of the sperm movement.

---

What is claimed is:

1. A method of contraception, comprising administering to a patient an effective dose of a zona pellucida peptide, wherein the peptide does not elicit an immunocontraceptive effect.

2. The method of claim 1, wherein the peptide is from a mouse or human ZP1, 2 or 3 protein.

3. The method of claim 1, wherein the peptide is from a mouse or human Z3 protein.

4. The method of claim 1, wherein the peptide is

| -RYPRQGNVSS- | (SEQ ID NO:1), |
| -TPSPLPDPNSSPY- | (SEQ ID NO:2), |
| -SRNRRHVTDEADVT- | (SEQ ID NO:3), |
| -CSNSSSSQFQIHGPR- | (SEQ ID NO:4), |
| -TRKCHSSSYLVSLPQ- | (SEQ ID NO:5), |
| -SQFQIHGPRQ- | (SEQ ID NO:6), |
| -TPTPDQNASPY- | (SEQ ID NO:7), |
| -CGTPSHSRRQPHVMS- | (SEQ ID NO:8), |
| -SRNRRHVTEEADVT- | (SEQ ID NO:9), |
| -TRRCRTASHPVSASE- | (SEQ ID NO:10), | or

| -SRRQPHVMSQ- | (SEQ ID NO:11). |

5. The method of claim 1, wherein the peptide further comprises an acetylated N-terminus and/or an amidated C-terminus.

6. The method of claim 1, wherein the peptide is produced synthetically.

7. The method of claim 1, wherein the peptide is administered intravenously, intramuscularly, subcutaneously, subdermally, transdermally, topically or orally.

8. The method of claim 1, wherein the peptide is formulated as a microcapsule, a salt, a biogradable implant, a liposome, a TDS, a mucous membrane-adhesive system, a cream, a gel or an ointment.

9. The method of claim 1, wherein the peptide is administered by ionophoresis.

10. The method of claim 1, wherein the patient is human.

11. The method of claim 1, wherein the peptide comprises at least 10 amino acids.

12. The method of claim 1, wherein the peptide has about 10 to 15 amino acids.

13. The method according to claim 1, wherein the peptide is specific for a zona pellucida protein.

14. A peptide

| | |
|---|---|
| -RYPRQGNVSS- | (SEQ ID NO:1), |
| -TPSPLPDPNSSPY- | (SEQ ID NO:2), |
| -SRNRRHVTDEADVT- | (SEQ ID NO:3), |
| -TGXCHSSSYLVSLPQ- | (SEQ ID NO:5), |
| -SQFQIHGPRQ- | (SEQ ID NO:6), |
| -TPTPDQNASPY- | (SEQ ID NO:7), |
| -CGTPSHSRRQPHVMS- | (SEQ ID NO:8), |
| -SRNRRHVTEEADVT- | (SEQ ID NO:9), | or

| | |
|---|---|
| -TRRCRTASHPVSASE- | (SEQ ID NO:10). |

15. A peptide of claim 14, which further comprises an acetylated N-terminus and/or an amidated C-terminus.

* * * * *

UNITED STATES PATENT AND TRADEMARK OFFICE
CERTIFICATE OF CORRECTION

PATENT NO. : 6,344,442 B2
APPLICATION NO. : 09/194062
DATED : February 5, 2002
INVENTOR(S) : Habenicht et al.

It is certified that error appears in the above-identified patent and that said Letters Patent is hereby corrected as shown below:

Column 13, line 12 reads "-TGXCHSSSYLVSLPQ-" should read
-- -TRKCHSSSYLVSLPQ- --

Signed and Sealed this

Fifteenth Day of August, 2006

JON W. DUDAS
*Director of the United States Patent and Trademark Office*

SEQUENCE LISTING

<160> NUMBER OF SEQ ID NOS: 12

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: synthetic
      peptide derived from murine or homo sapiens origin

<400> SEQUENCE: 1

Arg Tyr Pro Arg Gln Gly Asn Val Ser Ser
 1               5                  10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: synthetic
      peptide derived from murine or homo sapiens origin

<400> SEQUENCE: 2

Thr Pro Ser Pro Leu Pro Asp Pro Asn Ser Ser Pro Tyr
 1               5                  10

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: synthetic
      peptide derived from murine or homo sapiens origin

<400> SEQUENCE: 3

Ser Arg Asn Arg Arg His Val Thr Asp Glu Ala Asp Val Thr
 1               5                  10

<210> SEQ ID NO 4
<211> LENGTH: 15
<212> TYPE: PRT
<213> ORGANISM: Artificial Sequence
<220> FEATURE:

-continued

<223> OTHER INFORMATION: Description of Artificial Sequence: synthetic
      peptide derived from murine or homo sapiens origin

<400> SEQUENCE: 4

Cys Ser Asn Ser Ser Ser Ser Gln Phe Gln Ile His Gly Pro Arg
 1               5                  10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: synthetic
      peptide derived from murine or homo sapiens origin

<400> SEQUENCE: 5

Thr Arg Lys Cys His Ser Ser Ser Tyr Leu Val Ser Leu Pro Gln
 1               5                  10                  15

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: synthetic
      peptide derived from murine or homo sapiens origin
<220> FEATURE:
<223> OTHER INFORMATION: This peptide may be N-terminus acetylated (Ac)
      and c-terminus amidated (CONH2)

<400> SEQUENCE: 6

Ser Gln Phe Gln Ile His Gly Pro Arg Gln
 1               5                  10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: synthetic
      peptide derived from murine or homo sapiens origin

<400> SEQUENCE: 7

Thr Pro Thr Pro Asp Gln Asn Ala Ser Pro Tyr
 1               5                  10

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: synthetic
      peptide derived from murine or homo sapiens origin
<220> FEATURE:
<223> OTHER INFORMATION: This peptide may be N-terminus acetylated (Ac)
      and c-terminus amidated (CONH2)

<400> SEQUENCE: 8

Cys Gly Thr Pro Ser His Ser Arg Arg Gln Pro His Val Met Ser
 1               5                  10                  15

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: synthetic
      peptide derived from murine or homo sapiens origin

```
<400> SEQUENCE: 9

Ser Arg Asn Arg Arg His Val Thr Glu Glu Ala Asp Val Thr
  1               5                  10

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: synthetic
      peptide derived from murine or homo sapiens origin

<400> SEQUENCE: 10

Thr Arg Arg Cys Arg Thr Ala Ser His Pro Val Ser Ala Ser Glu
  1               5                  10                  15

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: synthetic
      peptide derived from murine or homo sapiens origin

<400> SEQUENCE: 11

Ser Arg Arg Gln Pro His Val Met Ser Gln
  1               5                  10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: synthetic
      peptide derived from murine or homo sapiens origin
<220> FEATURE:
<223> OTHER INFORMATION: This peptide is N-terminus acetylated (Ac)
      and c-terminus amidated (CONH2)

<400> SEQUENCE: 12

Gln Arg Pro Gly His Ile Gln Phe Gln Ser
  1               5                  10
```